United States Patent
Lai et al.

(10) Patent No.: US 7,602,672 B2
(45) Date of Patent: Oct. 13, 2009

(54) QUASI-SELF FOCUSING HIGH INTENSITY AND LARGE POWER ULTRASONIC TRANSDUCER

(75) Inventors: Ninglei Lai, Room 1504, Building No. 4, Yangguang Square, Longjiang Community, Nanjing City (CN) 210000; Qiji Lai, Nanjing (CN); Kefan Liu, Nanjing (CN); Guogan Xiong, Nanjing (CN)

(73) Assignee: Ninglei Lai, Nanjing (CN)

(*) Notice: Subject to any disclaimer, the term of this patent is extended or adjusted under 35 U.S.C. 154(b) by 175 days.

(21) Appl. No.: 11/722,858

(22) PCT Filed: Dec. 27, 2004

(86) PCT No.: PCT/CN2004/001527

§ 371 (c)(1),
(2), (4) Date: Jun. 26, 2007

(87) PCT Pub. No.: WO2006/069467

PCT Pub. Date: Jul. 6, 2006

(65) Prior Publication Data

US 2008/0112582 A1      May 15, 2008

(51) Int. Cl.
*H04B 1/02*      (2006.01)
(52) U.S. Cl. .................................................. 367/138
(58) Field of Classification Search ............... 367/138
See application file for complete search history.

(56) References Cited

U.S. PATENT DOCUMENTS

| 5,101,133 | A | 3/1992 | Schafer |
| 5,743,862 | A * | 4/1998 | Izumi ........................ 601/2 |
| 6,506,171 | B1 | 1/2003 | Vitek et al. |
| 2004/0201326 | A1* | 10/2004 | Yokoi et al. ............ 310/348 |

FOREIGN PATENT DOCUMENTS

| CN | 2370887 Y | 3/2000 |
| CN | 1265929 | 9/2000 |
| CN | 1416922 | 5/2003 |
| CN | 1456128 | 11/2003 |
| CN | 1470299 | 1/2004 |
| CN | 2608035 Y | 3/2004 |
| WO | WO03/070105 A1 | 8/2003 |

OTHER PUBLICATIONS

Donald Ricketts, "Model for Piezoelectric Polymer Flexural Plate Hydrophone", Oct 1981, Acoustic Society of America pp. 929-935.*

* cited by examiner

*Primary Examiner*—Thomas H Tarcza
*Assistant Examiner*—Luke D Ratcliffe
(74) *Attorney, Agent, or Firm*—Schwabe, Williamson & Wyatt, P.C.

(57) ABSTRACT

A quasi-self focusing high strength large power ultrasonic transducer including a backing and a plurality of piezo-electric crystal sheets is disclosed. The backing has a double layer structure with an air cavity between the layers. At least four piezoelectric crystal sheets of the plurality of piezo-electric crystal sheets are adhered on an inside focusing face of the backing with a protective layer covering the surface of the sheets.

9 Claims, 1 Drawing Sheet

QUASI-SELF FOCUSING HIGH INTENSITY AND LARGE POWER ULTRASONIC TRANSDUCER

This is a national stage entry of, and claims priority to, International Application PCT/CN2004/001527 titled "QUASI-SELF FOCUSING HIGH INTENSITY AND LARGE POWER ULTRASONIC TRANSDUCER" filed Dec. 27, 2004, the entire contents of which are hereby incorporated by reference in their entirety.

FIELD OF THE INVENTION

The present invention relates to an ultrasonic transducer, in particular, a high intensity large power ultrasonic transducer required for non-invasive true shape tumor therapy.

DESCRIPTION OF THE PRIOR ART

Ultrasonic transducer is the core component of high intensity focusing ultrasound tumor therapy system (HIFU), and its characteristics determine, to a large extent, the effectiveness, safety and high efficiency of HIFU treatment. However, as the necessary foundation for high quality medical equipment, "effectiveness, safety and high efficiency" pose a dilemma that is technically difficult for coordination and self-consistency. The focusing ultrasonic transducers currently used for HIFU tumor therapy include the following types. The first type is composed of plane piezoelectric ceramics sheets that focus through sound lens structure. This type of ultrasonic transducer was adopted in the No. 02113721.8 patent of invention under the title of "Ultrasonic Scalpel For Tumor Therapy" (publication number: CN1456128A), for which Microlife Medical Co., Ltd filed an application with SIPO on May 10, 2002. The second type is composed of small caliber piezoelectric ceramic sheets densely distributed in large quantity, which are embedded in large caliber rigid material with concave spherical zone surface in a disordered or ordered fashion. This type of ultrasonic transducer was used in No. 99102923.2 patent of invention under the title of "Ultrasonic Power Transmitter for Focused Extracorporeal Pyrotherapy Machine", for which Beijing Beiyi Medical Equipment Factory filed an application with SIPO on Mar. 9, 1999. This type of ultrasonic transducer was also adopted in No. 99206768.5 patent of utility model under the title "Multiple-focus Multiple Focusing Ultrasonic Transducer" (publication number: CN2370887Y), for which Qian Xianwei filed application with SIPO on Apr. 15, 1999. The third type is composed of small quantity of medium-caliber piezoelectric ceramic sheets or transducers (generally in circular shape), which are distributed on the large caliber rigid material with a concave spherical zone surface or on the equivalent curved space that has a radius of curvature identical to theirs. This type of ultrasonic transducer was used in No. 0328743.7 patent of utility model under the title of "Multiple-focus Multiple Focusing Ultrasonic Transducer" (publication number: CN2608035Y), for which Shanghai A&S Science Technology Development Co., Ltd. filed an application with SIPO on Feb. 11, 2003. The fourth type is composed of small quantity of piezoelectric ceramic sheets that are tightly scarf jointed on the convex back of acoustic radiation layer with a spherical zone surface. This type of ultrasonic transducer was used in No. 03 129407.3 patent of invention under the title "Transducer Array for High Intensity Focused Ultrasonic Tumor Therapy" (with publication number: CN1470299A), for which Shanghai Jiaotong University and Wuxi Haiying Electronic Medical System Co., Ltd. filed an application with SIPO on Jun. 19, 2003. All the above types of transducers are provided with relatively large holes for the installation of a type-B ultrasonic probe, thus reducing the effective sound emission area of the transducer, lowering the sound power, and deteriorating the sound field characteristics.

In addition, the electroacoustical efficiencies of the first and the fourth types of transducers are affected by the sound attenuation of the lens layer or radiating layer to varying degrees as well as by inadequate matching, so it is difficult for them to be made into high efficiency high-power transducers. To obtain better focusing characteristic, the second type of transducers require a great number of matrix elements (from hundreds of pieces to even over 1000 pieces), thus posing a higher demand for the multi-way high frequency or radio-frequency power supply performance of piezoelectric crystal sheets to be consistent or compatible in the actual production. As a result, the system is less reliable while the complexity increases. Due to their distribution characteristics of discrete matrix elements, the third type of transducers has relatively poor focusing performance and cohesive energy ratios. When applied in HIFU therapy, these types of transducers have had problems of coordination and self-consistency in terms of "effectiveness, safety and high efficiency", which are not solvable from time to time. As universally held in the industry, large-caliber self-focusing ultrasonic transducers with continuous concave can achieve the best performance of focusing sound field, high cohesive energy ratio, large ultrasonic power, high acoustoelectric conversion efficiency and focus sound intensity. However, due to great difficulty in manufacturing technology, no such type of transducer has been applied in the practical HIFU therapy system.

SUMMARY OF INVENTION

The purpose of the present invention: With regard to various problems encountered by the practical application of several types of ultrasonic transducer used in the high intensity focusing ultrasonic tumor therapy system (HIFU) for tumor treatment, provide a new quasi-self-focusing high intensity large power ultrasonic transducer.

The purpose of the present invention is achieved in this way: a quasi-self-focusing high strength large power ultrasonic transducer including a backing and piezo-electric crystal sheets, wherein the backing has a double-layer structure and there is an air cavity between the layers; at least four piezo-electric crystal sheets are adhered tightly on the inside focusing face of the backing; a protective layer is covered on the surface of the sheets.

The inside focusing face of the backing may be a concave spherical zone surface, and the thickness of inner layer of the backing is the integral multiple ±35% of ½ of the wavelength $\lambda$ of sound wave in the backing material under a specific working frequency emitted by the piezo-electric crystal sheets; 4~24 piezo-electric crystal sheets of similar electroacoustical characteristics, with the radius of curvature at all points identical to that of the corresponding points of inside focusing face of the backing, are adhered tightly on the inside focusing face of the backing.

When the caliber of the concave spherical zone surface of the inside face of the backing is selected as 160~200 ram, there are 4~8 pieces of the said piezo-electric crystal sheets. When the caliber of concave spherical zone surface of the inside face of the backing is selected as 200~500 ram, there are 6~24 pieces of the said piezo-electric crystal sheets.

A hole for providing cooling water for the working face may be disposed on the central spherical zone surface of the backing.

A hole for providing a power feed for the piezo-electric crystal sheets and a hole for providing cooling water for the working face may be simultaneously disposed on the central spherical zone surface of the backing.

The advantages of the present invention are as follows: since the backing is made of material with a low loss and high acoustic resistance, an air cavity is set up in the backing, the inside focusing face of the backing is shaped as concave sphere, and the thickness of the inner layer of the backing is selected as approximately the integral multiple of ½ of the wavelength λ in the backing material, the efficiency of front ultrasonic emission can be maximized. Because the spherical zone surface sector piezo-electric crystal sheets are tightly adhered to the inner surface of backing material, the type B ultrasonic probe hole is no longer needed on the central spherical zone surface of backing. Therefore, it is possible to achieve a focusing performance very similar to that of a large caliber spherical cap surface with a high cohesive energy ratio, and to achieve very high sound power and sound intensity. A hole for providing the working face with cooling water may be set up on the central spherical zone surface of the backing, thus greatly improving the operating environment and load-carrying capacity of the piezo-electric crystal sheets. According to tests, the present invention has a good sound field performance, very low longitudinal and transversal sound intensity side bands, a large enough caliber to focus ratio and good robustness.

Where: 1 denotes piezo-electric crystal sheets, 2 denotes protective layer, 3 denotes backing, 4 denotes air cavity, and 5 denotes a hole for providing the working face with cooling water.

DETAILED DESCRIPTION OF THE PREFERRED EMBODIMENTS

The Figures disclose the schematic diagrams relating to the specific embodiments of the present invention in a nonrestrictive manner. A further description of the present invention is given below in combination with the Figures.

Figure 1:
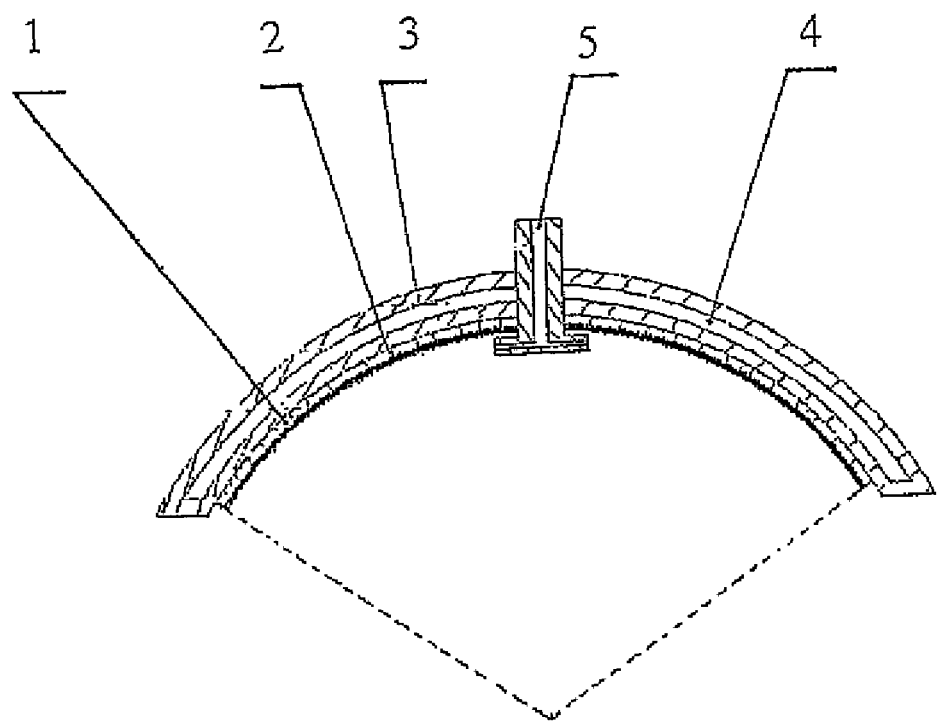
FIG. 1 is the structural representation of an embodiment of the present invention.

As shown in FIG. 1, embodiments of the present invention includes a backing 3 and piezo-electric crystal sheets 1; the backing 3 has a double-layer structure and there is an air cavity 4 between the layers; at least four piezoelectric crystal sheets 1 are adhered tightly on the inside focusing face of the backing 3. A protective layer 2 covers the surface of the crystal sheets 1. In the specific embodiments, the inside focusing face of said backing 3 may be a concave spherical zone surface, and the thickness of the inner layer of the backing 3 may be determined according to the following principle: under the specific working frequency emitted by the piezo-electric crystal sheets 1, the thickness is the integral multiple ±35% of the ½ of the wavelength λ of sound wave in the backing material. The piezo-electric crystal sheets 1, which are adhered tightly on the inside focusing face of the backing 3, shall have similar electroacoustical characteristics; furthermore, the radius of curvature at each point shall be identical to that of the corresponding points on the inside focusing face of the backing; the suitable quantity of piezo-electric crystal sheets is 4~24 pieces; a hole 5 for providing the working face with cooling water may be disposed on the central spherical zone surface of the backing 3, or a hole for providing power feed for piezo-electric crystal sheets 1 may be simultaneously disposed on the central spherical zone surface of the backing 3. In this embodiment, only a hole 5 for providing the working face with cooling water is disposed on the central spherical zone surface of the backing 3.

Figure 2:
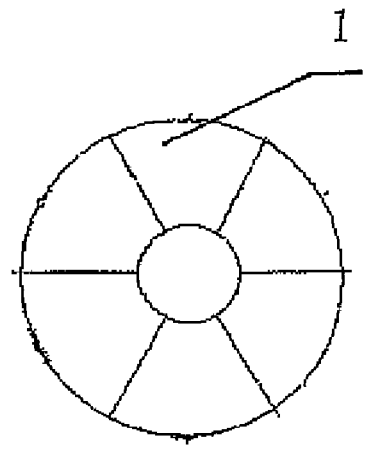
FIG. 2 is the embodiment of a mode in which the piezo-electric crystal sheets are arranged on the inside focusing face of backing.
Figure 3:
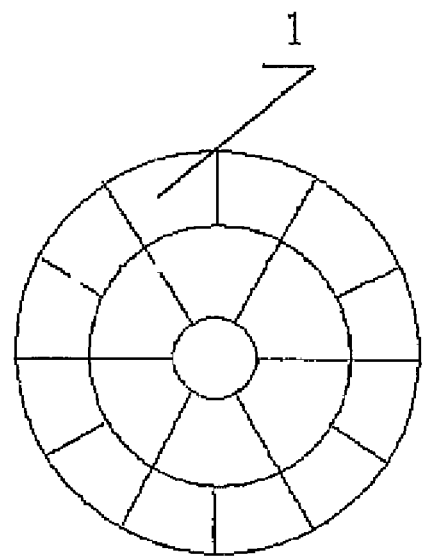
FIG. 3 is the embodiment of another mode in which the piezo-electric crystal sheets are arranged on the inside focusing face of backing.

When the caliber of the concave spherical zone surface of inside face of the backing 3 is selected as 160~200 mm, there are 4~8 pieces of said piezo-electric crystal sheets. When the caliber of the concave spherical zone surface of inside face of the backing is selected as 200~500 mm, there are 6~24 pieces of said piezo-electric crystal sheets. In the specific embodiment, when the caliber of concave spherical zone surface of the inside face of backing is relatively small, piezo-electric crystal sheets may be arranged in a single circle. The embodiment shown in FIG. 2 is the arrangement mode of 6 piezo-electric crystal sheets 1. When the caliber of the concave spherical zone surface of inside face of the backing 3 is relatively large, the piezo-electric crystal sheets may be arranged in multiple circles. The embodiment shown in FIG. 3 is the mode in which 18 piezo-electric crystal sheets 1 are arranged in two circles.

The invention claimed is:

1. A quasi-self focusing ultrasonic transducer including a backing; and
a plurality of piezo-electric crystal sheets,
wherein:
the backing has a double layer structure and there is an air cavity between the layers,
at least four piezo-electric crystal sheets of the plurality of piezo-electric crystal sheets are adhered on an inside focusing face of the backing,
a protective layer covers a surface of the sheets;
said backing is made of a material with low loss and high acoustic resistance;
the inside focusing face of the backing is a concave spherical zone surface;
a thickness of an inner layer of the backing is an integral multiple ±35% of ½ of a wavelength of a sound wave in the backing material under a working frequency emitted by the piezo-electric crystal sheets; and
the plurality of piezo-electric crystal sheets comprise between 4 and 24 piezo-electric crystal sheets of similar electroacoustical characteristics, with a radius of curvature at all points substantially identical to that of corresponding points of the inside focusing face of the backing, the between 4 and 24 piezo-electric crystal sheets being adhered on the inside focusing face of the backing.

2. The ultrasonic transducer of claim 1, wherein: a caliber of the concave spherical zone surface of the inside focusing face of the backing is between 160 and 200 mm, and wherein the plurality of piezo-electric crystal sheets comprise between 4 and 8 piezo-electric crystal sheets.

3. The ultrasonic transducer of claim 1, wherein: a caliber of the concave spherical zone surface of the inside face of the backing is between 200 and 500 mm and wherein the plurality of piezo-electric crystal sheets comprise between 6 and 24 piezo-electric crystal sheets.

4. The ultrasonic transducer of claim 3, further comprising a hole on a central spherical zone surface of the backing for providing cooling water for a working face.

5. The ultrasonic transducer of claim 3, further comprising a first hole for providing power feed to the plurality of piezoelectric crystal sheets on a central spherical zone surface of the backing and a second hole for providing cooling water for a working face on the central spherical zone surface of the backing.

6. The ultrasonic transducer of claim 2, further comprising a hole on a central spherical zone surface of the backing for providing cooling water for a working face.

7. The ultrasonic transducer of claim 2, further comprising a first hole for providing power feed to the plurality of piezoelectric crystal sheets on a central spherical zone surface of the backing and a second hole for providing cooling water for a working face on the central spherical zone surface of the backing.

8. The ultrasonic transducer of claim 1, further comprising a hole on a central spherical zone surface of the backing for providing cooling water for a working face.

9. The ultrasonic transducer of claim 1, further comprising a first hole for providing power feed to the plurality of piezoelectric crystal sheets on a central spherical zone surface of the backing and a second hole for providing cooling water for a working face on the central spherical zone surface of the backing.

* * * * *